United States Patent [19]
Phillips

[11] Patent Number: 5,549,714
[45] Date of Patent: Aug. 27, 1996

[54] SYMES FOOT PROSTHESIS

[76] Inventor: Van L. Phillips, P.O. Box 1873, Rancho Santa Fe, Calif. 92067

[21] Appl. No.: 371,595

[22] Filed: Jan. 12, 1995

Related U.S. Application Data

[63] Continuation of Ser. No. 103,732, Aug. 6, 1993, abandoned, which is a continuation of Ser. No. 844,898, Mar. 2, 1992, abandoned, which is a continuation of Ser. No. 585,920, Sep. 21, 1990, abandoned.

[51] Int. Cl.$^6$ ................................ A61F 2/66; A61F 2/80
[52] U.S. Cl. ............................................. 623/33; 623/55
[58] Field of Search .......................... 623/47–50, 52–56, 623/27–28, 33, 35

[56] References Cited

U.S. PATENT DOCUMENTS

| 61,780 | 2/1867 | Watson ..................................... 623/53 |
| 65,187 | 5/1867 | Emery . |
| 277,562 | 5/1883 | Furrer . |

(List continued on next page.)

FOREIGN PATENT DOCUMENTS

| 800547 | 7/1936 | France . |
| 1558440 | 12/1967 | France . |
| 2085624 | 12/1970 | France . |
| 25322 | 10/1972 | France . |
| 2410998 | 6/1979 | France . |
| 2486388 | 7/1980 | France . |
| 2581859 | 11/1986 | France . |
| 295807 | 12/1916 | Germany . |
| 308671 | 10/1918 | Germany . |
| 325171 | 9/1920 | Germany . |
| 379849 | 8/1923 | Germany . |
| 807214 | 6/1951 | Germany . |
| 883321 | 7/1953 | Germany . |
| 179844 | 10/1954 | Germany . |
| 1179328 | 4/1957 | Germany . |
| 963849 | 5/1957 | Germany . |
| 1211354 | 2/1966 | Germany . |
| 2718395 | 9/1986 | Germany . |
| 454046 | 3/1988 | Sweden . |
| 0397204 | 9/1973 | U.S.S.R. .................................. 623/53 |
| 605613 | 4/1978 | U.S.S.R. . . |
| 1217404 | 3/1986 | U.S.S.R. . . |
| 1477401 | 5/1989 | U.S.S.R. .................................. 623/55 |
| 22172 | 9/1898 | United Kingdom . |
| 16750 | 12/1916 | United Kingdom . |

(List continued on next page.)

OTHER PUBLICATIONS

"The Seattle Prosthesis Foot—A Design for Active Sports: Preliminary Studies," E. M. Burgess, M.D., et al., *Orthotics and Prosthetics Journal*, vol. 37, No. 1, Spring 1983.
The Seattle Foot—Winner of Presidential Design Aware—Jan. 30, 1985.
Copes/Bionic Ankle.
L.A. Times View Section, "Seattle Foot," Jun. 12, 1984.
Campbell Childs, Jr. Product Catalog.
"The Flex–Shin: A Composite Material for Use in Flexible Shank Below–Knee Prosthesis," Thurston, et al., *Prosthetics and Orthotics International*.
"Experimentation Clinique D'Une Prothese De Membre Inferieur En Materiaux Composites,": Andre Gueyraud, *University of Marseille*, 1987.

Primary Examiner—David H. Willse
Attorney, Agent, or Firm—Knobbe, Martens, Olson & Bear

[57] ABSTRACT

A prosthetic foot is characterized by a forefoot portion incorporating an attachment section, a curvilinear ankle section, an arch section and a toe section, said ankle section being configured so that the foot may be worn by persons whose legs have been amputated at or near the wearer's ankle region. The foot further includes a heel portion secured to the forefoot portion. The foot is fabricated from polymer impregnated and encapsulated laminates, including such laminates as carbon fibers and/or fiberglass or synthetic fibers such as Kevlar. A preferably demountable connection of the heel portion to the forefoot portion permits interchangeability of those components to match the weight, stride and activity schedule of the wearer utilizing the prosthetic foot.

1 Claim, 2 Drawing Sheets

U.S. PATENT DOCUMENTS

| | | |
|---|---|---|
| 366,494 | 7/1887 | Marks . |
| 693,400 | 2/1902 | Jochimsen . |
| 708,685 | 9/1902 | White . |
| 809,875 | 1/1906 | Wilkins . |
| 817,340 | 1/1906 | Rosenkranz . |
| 827,720 | 8/1906 | Erwin . |
| 951,989 | 3/1910 | Hanger . |
| 1,013,828 | 1/1912 | Thomas . |
| 1,071,230 | 8/1913 | Hanger . |
| 1,128,018 | 2/1915 | McFarland . |
| 1,151,144 | 8/1915 | Wofe et al. . |
| 1,294,632 | 2/1919 | Dickson . |
| 1,352,943 | 9/1920 | Dodge . |
| 1,424,264 | 8/1922 | Shrodes . |
| 1,804,915 | 5/1931 | Collins . |
| 2,036,830 | 4/1936 | Rowley . |
| 2,075,583 | 3/1937 | Lange . |
| 2,126,654 | 8/1938 | Morris . |
| 2,197,093 | 4/1940 | Campbell . |
| 2,379,538 | 7/1945 | Meierhofer . |
| 2,440,075 | 4/1948 | Campbell . |
| 2,453,969 | 11/1948 | Carter . |
| 2,475,372 | 7/1949 | Catranis . |
| 2,543,908 | 3/1951 | Guzey . |
| 2,556,525 | 6/1951 | Drennon . |
| 2,570,735 | 10/1951 | Weise . |
| 2,619,652 | 12/1952 | Vesper . |
| 2,692,392 | 10/1954 | Bennington . |
| 2,699,554 | 1/1955 | Comelli . |
| 2,899,685 | 8/1959 | Boucier de Carbon . |
| 3,206,235 | 9/1965 | Albinson et al. . |
| 3,335,428 | 5/1967 | Gajdos . |
| 3,400,408 | 9/1968 | Garcia . |
| 3,414,908 | 12/1968 | Waggott et al. . |
| 3,422,462 | 1/1969 | Finnieston . |
| 3,438,587 | 4/1969 | Jackson, Jr. . |
| 3,538,516 | 11/1970 | Bailey et al. . |
| 3,659,294 | 5/1972 | Glabiszewski . |
| 3,707,731 | 1/1973 | Morgan . |
| 3,754,286 | 8/1973 | Ryan . |
| 3,833,941 | 9/1974 | Wagner . |
| 3,874,004 | 4/1975 | May . |
| 3,889,301 | 6/1975 | Bonner, Sr. . |
| 3,890,650 | 6/1975 | Prahl . |
| 3,953,900 | 3/1976 | Thompson . |
| 3,982,278 | 9/1976 | May . |
| 4,007,496 | 2/1977 | Glabiszewski . |
| 4,074,542 | 2/1978 | Hankosky et al. . |
| 4,089,072 | 5/1978 | Glabiszewski . |
| 4,091,472 | 5/1978 | Daher et al. . |
| 4,128,903 | 12/1978 | Marsh et al. . |
| 4,161,042 | 7/1979 | Cottingham et al. . |
| 4,177,525 | 12/1979 | Arbogast et al. . |
| 4,180,872 | 1/1980 | Chaikin . |
| 4,186,449 | 2/1980 | Horvath . |
| 4,216,550 | 8/1980 | Thompson . |
| 4,225,982 | 10/1980 | Cochrane et al. . |
| 4,268,922 | 5/1981 | Marsh et al. . |
| 4,302,856 | 12/1981 | May . |
| 4,306,320 | 12/1981 | Delp . |
| 4,314,398 | 2/1982 | Pettersson . |
| 4,328,594 | 5/1982 | Campbell et al. . |
| 4,360,931 | 11/1982 | Hampton . |
| 4,370,761 | 2/1983 | Serri . |
| 4,395,783 | 8/1983 | Eyre et al. . |
| 4,397,048 | 8/1983 | Brown et al. . |
| 4,459,709 | 7/1984 | Leal et al. . |
| 4,506,395 | 3/1985 | Haupt . |
| 4,536,898 | 8/1985 | Palfray . |
| 4,547,913 | 10/1985 | Phillips ................................. 623/27 |
| 4,608,054 | 8/1986 | Schroder . |
| 4,619,661 | 10/1986 | Axelsson . |
| 4,636,220 | 1/1987 | Ziegelmeyer . |
| 4,645,509 | 2/1987 | Poggi et al. . |
| 4,652,266 | 3/1987 | Truesdell . |
| 4,676,800 | 6/1987 | Chen . |
| 4,676,801 | 6/1987 | Lundeen . |
| 4,721,510 | 1/1988 | Cooper et al. . |
| 4,728,336 | 3/1988 | Cooper . |
| 4,792,340 | 12/1988 | Aulie et al. . |
| 4,822,363 | 4/1989 | Phillips ................................. 623/27 |
| 4,865,612 | 9/1989 | Arbogast et al. . |
| 4,883,493 | 11/1989 | Martel et al. . |
| 4,883,494 | 11/1989 | Cooper . |
| 4,892,553 | 1/1990 | Prahl . |
| 4,892,554 | 1/1990 | Robinson . |
| 4,911,724 | 3/1990 | Fikes . |
| 4,923,475 | 5/1990 | Gosthnian et al. . |
| 4,938,776 | 7/1990 | Masinter ............................... 623/49 |
| 4,938,777 | 7/1990 | Mason et al. . |
| 4,959,073 | 9/1990 | Merlette ................................. 623/55 |
| 4,969,911 | 11/1990 | Greene . |
| 4,994,086 | 2/1991 | Edwards . |
| 5,004,477 | 4/1991 | Palfray . |
| 5,007,938 | 4/1991 | Prahl . |
| 5,013,325 | 5/1991 | Rennerfelt . |
| 5,019,109 | 5/1991 | Voisin . |
| 5,037,444 | 8/1991 | Phillips ................................. 623/53 |
| 5,062,859 | 11/1991 | Naeder . |
| 5,066,305 | 11/1991 | Firth . |
| 5,071,435 | 12/1991 | Fuchs et al. . |
| 5,108,454 | 4/1992 | Rothschild et al. . |
| 5,112,356 | 5/1992 | Harris et al. . |
| 5,116,381 | 5/1992 | Palfray . |
| 5,116,384 | 5/1992 | Wilson et al. . |
| 5,116,385 | 5/1992 | Allard et al. . |
| 5,156,631 | 10/1992 | Merlette . |
| 5,156,632 | 10/1992 | Wellershaus . |

FOREIGN PATENT DOCUMENTS

| | | |
|---|---|---|
| 120445 | 11/1917 | United Kingdom . |
| 120462 | 11/1918 | United Kingdom . |
| 275902 | 8/1927 | United Kingdom . |
| 306313 | 4/1928 | United Kingdom . |
| 621576 | 7/1946 | United Kingdom . |
| 1371996 | 10/1974 | United Kingdom . |
| 1432481 | 4/1976 | United Kingdom . |
| 2089216 | 6/1982 | United Kingdom . |
| 2092451 | 8/1982 | United Kingdom . |
| 2124493 | 2/1984 | United Kingdom . |
| 2202448 | 9/1988 | United Kingdom ................... 623/53 |
| 8800815 | 7/1986 | WIPO . |
| 8905617 | 12/1987 | WIPO . |
| 8909036 | 10/1989 | WIPO . |

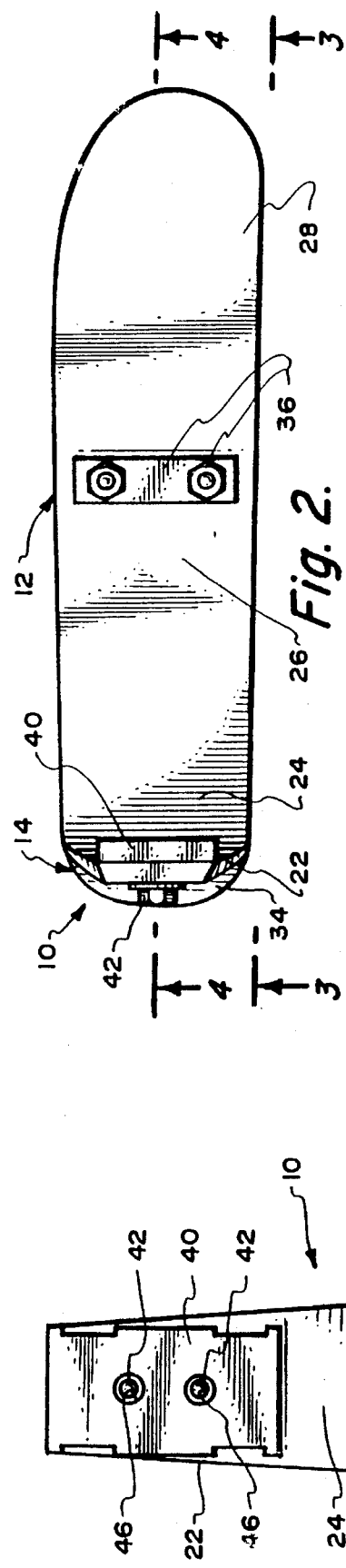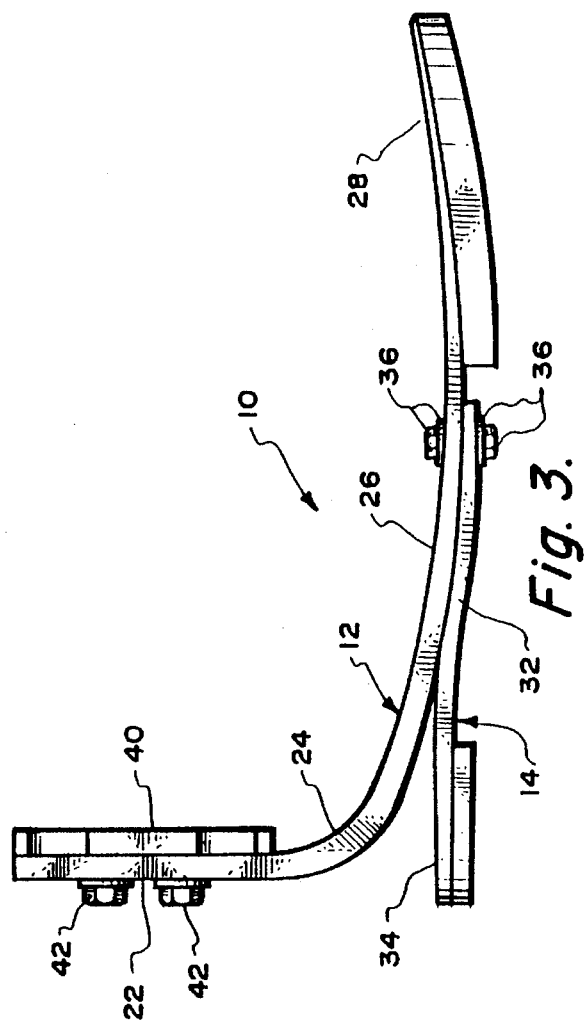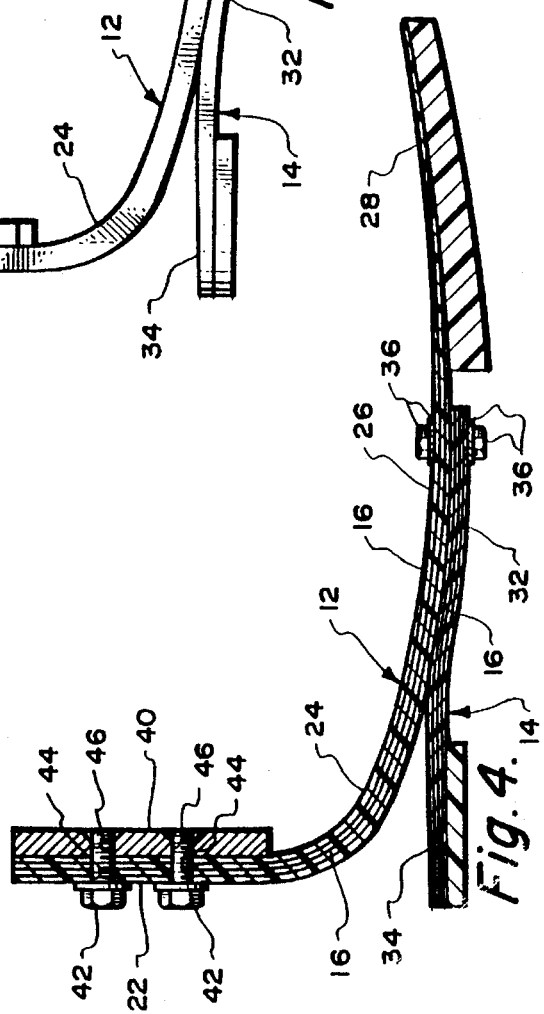

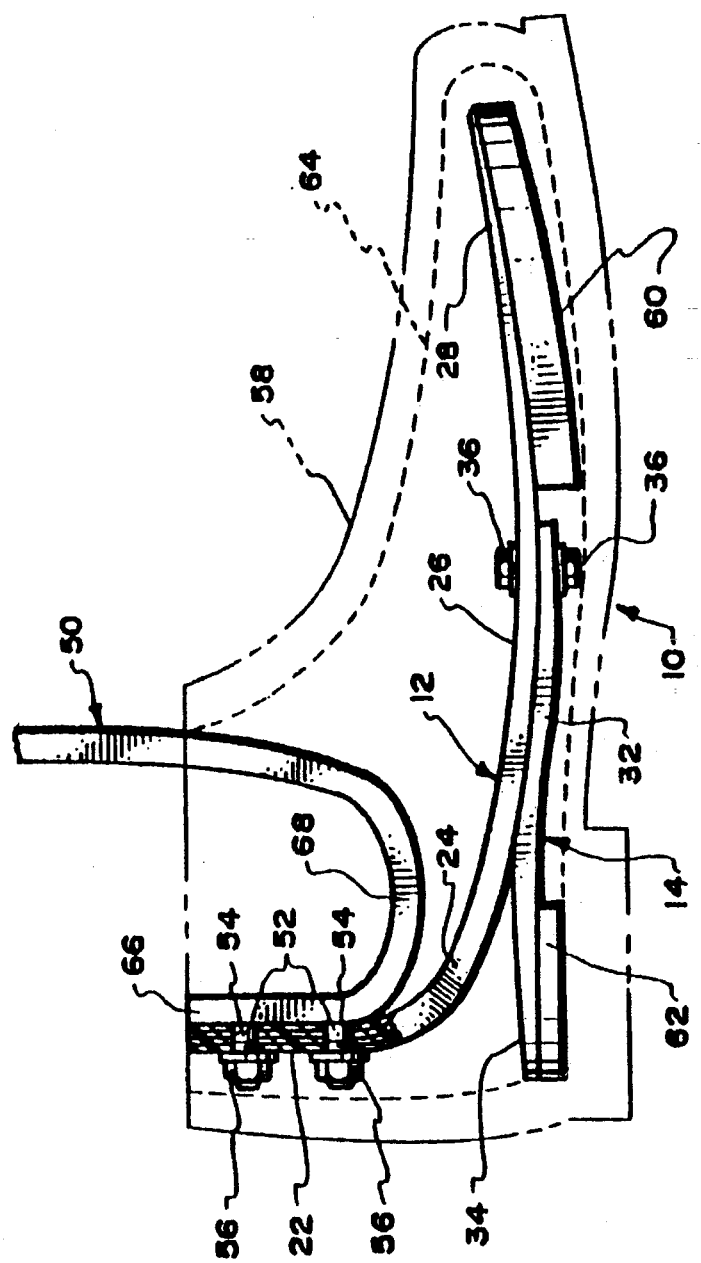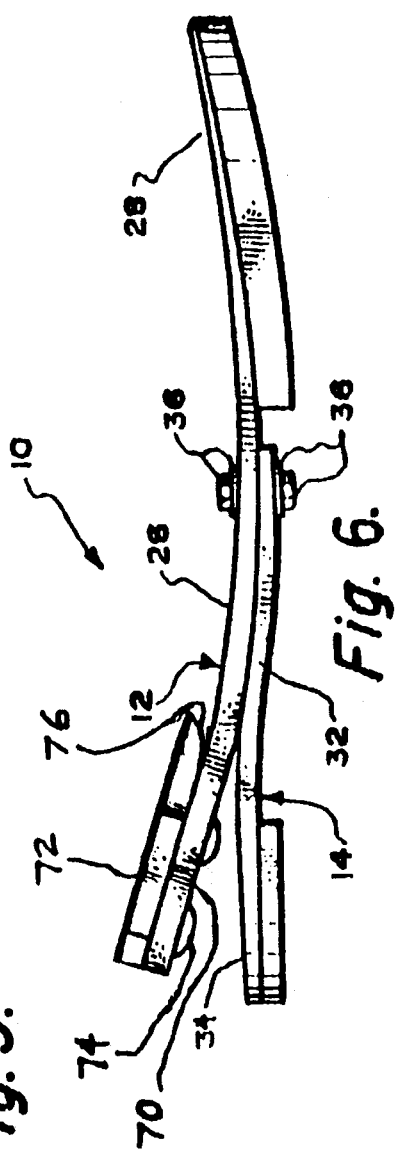

SYMES FOOT PROSTHESIS

RELATED APPLICATIONS

This application is a continuation of U.S. application Ser. No. 08/103,732 filed Aug. 6, 1993, now abandoned, which is a continuation of U.S. application Ser. No. 07/844,898 filed Mar. 2, 1992, now abandoned, which is a continuation of U.S. application Ser. No. 07/585,920 filed Sep. 21, 1990, now abandoned.

BACKGROUND OF THE INVENTION

This invention relates to foot prostheses in general, and specifically to a prosthetic foot adapted for use by persons who have undergone what is known in the art as a Symes amputation. This amputation severs the foot from the leg near the ankle region. Because the Symes patient's calf and shin functions as the patient's stump for prosthetic purposes, any prosthetic device utilized by the patient must either be relatively compact so as to be attachable below the point of amputation, or must be configured to accommodate the patient's shin and calf while attached thereto or higher up on the wearer's leg.

Prior art prostheses available to Symes patients typically include an artificial foot bonded or bolted onto the bottom end of a socket worn on the patient's stump. Examples of prior art Symes-type prostheses include U.S. Pat. No. 3,874,004 to May, which teaches an artificial ankle joint which can pivot in simulation of a natural ankle, and U.S. Pat. No. 4,225,982 to Cochrane, which teaches an elongated socket secured to a rubber-filled cavity of a slipper member.

Other prosthetic foot devices include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

These and other prosthetic foot devices, however, have significant deficiencies; for example, the May '004 and the Cochrane '982 patents achieve relatively focused and limited stress response because of their structure and reliance on hardened rubber members for flexure. Moreover, the component parts of the prostheses are too heavy and too rigid, as in Lange, or are too massive and monolithic, as in Poggi, to respond properly to the nuances of stress-response gradients characteristic of the human foot.

Certain of these performance deficiencies are overcome in U.S. Pat. No. 4,547,913 for my invention relating to a "Composite Prosthetic Foot and Leg" and U.S. Pat. No. 4,822,363 for my invention relating to a "Modular Composite Prosthetic Foot and Leg". Also, my pending applications Serial Nos. 07/337,374 (now U.S. Pat. No. 5,181,932) and 07/293,824 (now U.S. Pat. No. 5,037,444) disclose prosthetic foot devices with similar preferred materials and methods of manufacture, and with corresponding benefits therefrom.

Each of my aforementioned inventions is characterized by lightweight, elongated structures incorporating polymer impregnation of superimposed reinforcing laminae maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

None of my prior inventions, however, is readily utilized by Symes amputees, because of the various constraints set forth above. Among other things, my prior prosthetic inventions are not configured to accommodate affixation to a Symes-type stump, in that the prostheses are not compact enough to be attachable below the point of amputation, nor are they configured to accommodate the patient's shin and calf while attached thereto or higher up on the wearer's leg.

OBJECTS AND ADVANTAGES OF THE INVENTION

It is, therefore, an object of my invention to provide a prosthetic foot suitable for use by Symes amputees, which foot incorporates the desirable lightweight, flexible, energy-absorbing and energy-storing performance of certain of my prior inventions.

It is a further object of my invention to provide a prosthetic foot of the aforementioned character which is of modular configuration, resulting in ready assembly and adjustability thereof. The foot of my invention preferably includes forefoot and heel portions that can be readily exchanged with correspondingly-constructed forefoot and heel portions to provide size adjustment or different spring rates to suit the size of foot of the amputee or the stride, height, weight, and activity level of the amputee. Therefore, a range of combinations of spring rate and size can be provided to the amputee, achieving a natural stride and resilience of gait, which has not been fully obtainable by prior art prosthetic devices.

Another object of the invention is the provision of a prosthetic foot of the aforementioned character in which the forefoot and heel portions of the prosthesis are fabricated from superimposed laminates maintained in operative relationship by an encapsulating polymer, and further in which said foot is susceptible to bending stress determined by the number of the laminates and polymers in the respective element. Thus, the laminates are encapsulated in a polymer and capable of spring stress response as loads are imposed thereupon during the utilization of said foot.

A further object of the invention is the provision of a prosthetic foot of the aforementioned character which consists of continuous, integrally and simultaneously formed attachment, ankle, arch and toe sections of said forefoot portion, and attachment and heel sections of said heel portion, said sections being fabricated as a unitary structure by polymer impregnation of superimposed reinforcing laminae maintained in the desired configuration of said foot and said sections being capable of spring stress generated energy storage whereby the subjection of the prosthetic foot to bending moments will cause uniform transmission of spring stress through said sections of said foot.

The polymers utilized to encapsulate the fibrous laminae are characterized by elasticity and flexibility so that the foot prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic foot, after proper fitting of the foot to insure that it is properly balanced and of appropriate size, the prosthesis may be encapsulated in a suitably shaped cosmetic shroud. The shroud must be sufficiently flexible so as not to inhibit the free movement and flexure of the foot, but, because of the inherently resilient and stress-absorbing characteristics of said foot, little dependence is needed upon the ancillary cushioning action of the shroud.

Consequently, the foot of my invention is characterized by extreme light weight, instantaneous response to imposed loads and correspondingly instantaneous delivery of stored energy when the gait of the wearer indicates that such stored energy is to be released. The wearer of the foot may engage in a wide variety of activities which were precluded in the past, or in activities in which the wearer's enjoyment was limited, because of the structural limitations and corresponding performance of prior art prostheses. Running, jumping and other activities are sustained by the foot and it may be utilized in substantially the same manner as the normal foot of the wearer.

Another object of my invention is to provide a prosthesis of the aforementioned character that may be completely or substantially disposed within the patient's shoe, thus providing an optimum cosmetic appearance.

Yet another object of my invention is the provision of a prosthetic foot of the aforementioned character which consists of continuous, integrally and simultaneously formed attachment, arch and toe sections of said forefoot portion, and attachment and heel sections of said heel portion.

An additional object of my invention is the provision of a prosthetic foot of the aforementioned character in which the aforedescribed forefoot and heel portions may be manufactured by various expedients, including injection molding and/or the use of thermoplastic materials and processes, or any of a range of combinations thereof.

Other objects and advantages of the invention will be apparent from the following specification and the accompanying drawings, which are for the purpose of illustration only.

BRIEF DESCRIPTION OF THE DRAWINGS

FIG. 1 is a front elevation view of a prosthesis constructed in accordance with the teachings of the invention;

FIG. 2 is a plan view of a prosthesis constructed in accordance with the teachings of the invention;

FIG. 3 is a side elevation view, taken along line 3—3 of FIG. 2;

FIG. 4 is a side elevation sectional view, taken along line 4—4 of FIG. 2;

FIG. 5 is a partially sectional side elevation view of an alternative embodiment of the prosthesis of the invention, similar to the view shown in FIG. 3; and FIG. 6 is a side elevation view of an alternative embodiment of the invention, similar to the view of FIG. 3.

DESCRIPTION OF THE PREFERRED EMBODIMENT

Referring to the drawings, and particularly to FIG. 3 thereof, I show a foot prosthesis 10 constructed in accordance with the teachings of the invention and including a forefoot portion 12 and a heel portion 14 secured thereto.

The forefoot portion 12 preferably includes an attachment section 22, a curvilinear ankle section 24, an arch section 26 and a toe section 28. The heel portion 14 preferably includes an attachment section 32 and a heel section 34 projecting rearwardly therefrom. The various sections of the forefoot and heel portions, respectively, are preferably formed integrally with one another and simultaneously by the incorporation of a plurality of laminae 16, FIG. 4, embedded in a hardened, flexible polymer, similar to the fabrication methods taught in my above-noted patents.

The forefoot and heel portions of my invention, as well as the inventions of my above-noted patents, may also be manufactured by various other expedients, including injection molding and/or the use of thermoplastic materials and processes, or any of a range of combinations thereof.

Among other things, chopped fiber may be blended in a thermoplastic or thermoset resin and the resulting mixture injection molded into an appropriate configuration. Alternatively or additionally, thermoplastic laminae may be wound around an injection-molded core, or a thermoplastic resin may be injected between thermoplastic or thermoset laminae, whereby the laminates are bonded onto the injected material.

The ankle section 24 of the forefoot portion 12, as best shown in FIGS. 3–5, is configured to permit juxtaposition thereof to a rearward surface 66 and a lower surface 68 of a socket associated with the wearer's stump. The ankle section has a sufficiently small radius of curvature to permit the aforesaid juxtaposition to the stump of the wearer. In other words, the radius of the ankle section 24 is contoured to accommodate the socket of the Symes amputee. It is estimated that radii in the range of approximately ¾ to b 1¾ inches are useful for providing both the desired accommodation of the socket and the desired energy-absorbing and energy-storing characteristics discussed herein.

The attachment section 32 of the heel portion 14 is preferably secured to the intersection of the curvilinear ankle section 24 and the arch section 26 of the forefoot portion 12. Such securement may be permanent, through the use of epoxy, glue or the like, or may be demountable, FIG. 3, through the utilization of bolt, nut and washer combinations 36 assembled through corresponding holes in the forefoot and heel portions 12 and 14. Demountable attachment is preferred, in that it permits said forefoot portion to be selectably affixed to any of various heel portions having different spring rates, as more fully discussed below.

As indicated above, the forefoot and heel portions 12 and 14 are preferably fabricated from superimposed laminates 16, FIG. 4, maintained in operative relationship by an encapsulating polymer and susceptible to bending stress determined by the thickness of the laminates. The preferred materials and fabrication process are more thoroughly described and explained in my above-mentioned U.S. Pat. Nos. 4,547,913 and 4,822,363, and include laminates such as carbon fibers and/or fiberglass or synthetic fibers such as Kevlar. Exemplary alternative methods and materials are described hereinabove.

The construction of the forefoot and heel portions 12 and 14 of my invention thus preferably includes continuous, integrally and simultaneously formed sections 22, 24, 26, and 28, and 32 and 34, respectively. The aforesaid sections are fabricated as unitary structures by polymer impregnation of the aforedescribed superimposed reinforcing laminae. As a result of the materials, design and construction of the prosthetic foot 10, the various sections are capable of spring stress generated energy storage whereby the subjection of the prosthetic foot of my invention to bending moments will cause transmission of spring stress through said sections.

It will be obvious to those skilled in the art that a virtually infinite variety of forefoot portions 12 and heel portions 14 may be fabricated, each having unique spring stress response characteristics determined by the configuration, composition and amount of the various component materials utilized therein. The aforementioned demountable connection of the heel portion to the forefoot portion therefore permits interchangeability of those portions to match the weight, stride and activity schedule of the wearer utilizing the prosthetic foot.

The foot 10 affixed to the wearer by any of several means. For example, an attachment plate 40, FIG. 4, may be secured to the attachment section 22 of the forefoot portion 12 through the use of threaded bolt means 42. The threaded bolts 42 are assembled through holes 44 in the attachment section 22 into correspondingly threaded holes 46 in the plate 40. The plate 40 may be laminated or otherwise affixed to a known Symes-type socket.

In an alternative method of attachment, FIG. 5, the prosthesis 10 is provided with a shorter attachment section 22. A socket member 50 is provided with threaded bolt extensions 52 suitably positioned to be inserted through corresponding holes 54 in the attachment section 22. Nut and washer combinations 56 are utilized to secure the socket in juxtaposition to the attachment section 22. The profile of the embodiment of FIG. 5 is so low that all or substantially all of the prosthetic foot 10 can be concealed in a shoe 58.

Those skilled in the art will understand that attachment means 40 have been described hereinabove merely by way of example, and that many alternative attachment means are available and may be utilized without departing from the scope of the invention.

The attachment section 22, when assembled with the attachment means 40, is substantially rigid and capable of sustaining torsional, impact, and other loads impressed thereupon by the wearer during use of the foot 10. In addition, the inherent rigidity of the attachment section prevents it from being distorted in any way and causes the effective transmission of the aforesaid loads imposed there--upon between the wearer and the prosthetic foot 10.

The forefoot and heel portions 12 and 14 can be provided with different numbers of laminates to make them more or less compliant to loads transmitted between the wearer and surface upon which the foot 10 is impacting. Consequently, when confronted with various anomalies in an amputee, such as an overweight condition or excess activity levels, the structure of the forefoot and heel portions can be materially modified to provide action which is precisely adjusted to the needs of the amputee. Moreover, a variety of forefoot and heel portions 12 and 14 can be made available to an amputee, allowing the flexibility of the prosthesis to be adjusted on the basis of the particular activity which the amputee is undertaking.

Pad members 60 and 62, FIG. 5, may be affixed to the underside of the forefoot and heel portions, to create a profile for the bottom of the prosthesis 10 which corresponds to the interior of a shoe. Such a profile orients the foot 10, when the foot is in an unstressed state, at an appropriate angle for wearing shoes.

A cosmetic shroud 64, FIG. 5, may be utilized to encapsulate the forefoot and 10, in a manner more fully explained in my previously-described patents.

Another example of an alternative embodiment of my invention is illustrated in FIG. 6, in which the heel portion 14 and the arch section 26 and toe section 28 of the forefoot portion 12 are substantially the same as those illustrated in FIGS. 1–5. In the embodiment of FIG. 6, however, an attachment section 70 is formed adjacent to and integrally with the arch section 26. Attachment means such as an attachment plate 72 and corresponding screws 74 are provided adjacent the attachment section 70 to provide affixation to the wearer's socket (not shown).

The structure and method of this attachment may include, for example, any of those described above regarding attachment means 40 of FIGS. 1–4 or socket member 50 of FIG. 5. As indicated in FIG. 6, however, the front edge 76 of the attachment plate 72 is preferably provided with a curvilinear surface to reduce stress concentration in that area during flexure of the prosthesis. In addition, to maximize the amount of flexure available with the prosthesis of FIG. 6, button-head screws or other low-profile attachment means are preferred. Higher profile attachment means have the disadvantage of contacting the heel section 34 during heavy loading, thus preventing desired further flexure of the components of the prosthesis.

Those skilled in the art will understand that auxiliary flexure members (not shown) such as those described and shown in my copending applications Ser. Nos. 07/293,824 (see FIG. 7 therein) and 07/337,374 may be efficaciously utilized in connection with any embodiment of the above-described invention, without departing from the scope of the teachings hereof.

In the preferred embodiment, the forefoot and heel portions 12 and 14 are constructed with some slight tapering of thickness along the length thereof, although those skilled in the art will understand that the invention is not limited to such tapering construction.

The materials from which the portions 12 and 14 are fabricated must be such as to provide an energy-storing, resilient, spring-like effect. This is necessary because each engagement of the prosthetic foot 10 with an adjacent surface impresses compression, torsional, and other loads upon the prosthesis which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The forefoot and heel portions 12 and 14 of the prosthesis are preferably molded as a unitary component and are carefully formed to provide for appropriate absorption of stress imposed thereupon. The configuration of elements 12 and 14 is of utmost importance and the laminates and the polymer or polymers from which the elements are fabricated must be resilient and capable of absorbing the compressive, torsional, and other stresses referred to hereinabove and of restoring the stored energy created by such stresses, in a natural manner, to the impacted surface which originally imposed such stresses upon the prosthesis 10.

It has been found that there is a limited number of polymers capable of sustaining the significant stresses and repetitive loads imposed upon the prosthesis 10, particularly in the light of the countless numbers of cycles to which the prosthesis 10 is subjected during normal, everyday use.

At present, the best materials for the prosthesis are a composite of high-strength graphite fiber in a high-toughness epoxy thermosetting resin system. There are several reasons for this: (1) high strength; (2) stiffness to weight ratio of graphite as compared to other materials; (3) the almost complete return of input or stored energy; (4) light weight; (5) high fatigue strength; and (6) minimal creep. As an alternative material, fiberglass/epoxy is a fair choice, but it is not as good as graphite because of lower fatigue strength and higher density. Kevlar is even less acceptable due to poor compression and shear strength, although it is the lowest density of those mentioned.

An important aspect of the polymers and laminates referred to hereinabove is that they are characterized by needed, but not excessive, flexural deflection under load, which characteristic permits the shock-absorption stress loading of the prosthesis 10 while maintaining sufficient stability to prevent the collapse of the prosthesis while loads are imposed thereupon.

To achieve the relatively thin construction of the forefoot and heel portions 12 and 14, the aforesaid polymers are utilized in conjunction with various laminating materials. Various types and various dimensions of fibrous laminae can be utilized to achieve the continuum required by the design of the elements 12 and 14 to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the mold to permit them to be encapsulated in the selected polymer.

Obviously, the number and thickness of the superimposed laminae and the lengths thereof, together with the thickness of the encapsulating polymer, determines the stress characteristics of the resultant elements 12 and 14 and, correspondingly, impacts the total weight of the prosthesis 10. As will be apparent from the discussion hereinbelow, the individual portions 12 and 14 are designed to specifically accommodate individuals having different foot sizes, different weights and different strides and the individual design of the portions 12 and 14 provides for matching, to an extent previously unknown in the art, the natural characteristics of the wearer's uninjured limb.

As previously mentioned, the attachment section 22, the ankle section 24, the arch section 26, and the toe section 28 of the forefoot portion 12 are formed integrally. Likewise, the attachment section 32 and the heel section 34 of the heel portion are formed integrally. The configuration of these sections is the means whereby bending and compressive loads imposed during impingement of the prosthetic foot 10 upon an adjacent surface are absorbed and subsequently reimposed upon said surface. These various sections are so designed that they function, substantially, to permit some flexure of the portions 12 and 14, in a manner analogous to a normal foot and normal ankle joint, permitting the wearer to experience a more natural gait and feel with the prosthesis than was possible with prior art Symes prostheses.

The forefoot portion of the alternative embodiment of FIG. 6 is similarly constructed in an integral manner. The lower profile of the embodiment of FIG. 6 permits a more effective cosmetic shrouding of the prosthesis and more complete coverage of the prosthesis by a shoe.

The prosthetic foot of my invention can thus be provided in different sizes to correspond to the size of the natural foot of the wearer of the prosthesis 10. When such different sizes are provided, corresponding reduction or increase in the number of laminae and thickness of taper, if any, of the respective sections of the forefoot and heel portions 12 and 14 can be made to provide for the proper flexure of said sections.

Moreover, the flexibility of the prosthetic foot of my invention may be further increased, while still maintaining acceptable strength characteristics, by providing an auxiliary ankle member or an auxiliary forefoot portion (not shown, but similar to that illustrated in my copending application Ser. No. 07/337,374). Such an auxiliary member or portion would be operatively affixed to the forefoot portion 12 to provide some relative movement therebetween.

By such a construction, the same total thickness of supportive material is achieved in an assembly of overlying, juxtaposed, thin layers, which construction has much more flexibility than does a unitary forefoot portion of the same total material thickness. Such an auxiliary support member can be especially beneficial in the construction of FIG. 6.

It will, of course, be obvious to those skilled in the art that, with respect to any embodiment of the invention, the fibrous reinforcements in the form of laminae plies encapsulated in the prosthesis may be fayed or tapered to accomplish a gradual transition in the flexural characteristics of the prosthesis as the number of plies is reduced in any area of the prosthesis.

Moreover, if a individual partakes in sports or other activities which subject the prosthesis 10 to greater loads than those of normal daily wear, a prosthesis will be fitted which will accommodate for those greater loads.

Because the various sections 22, 24, 26, and 28, and 32 and 34, respectively, of the foot 10 are integrally fabricated, the aforesaid stresses are distributed throughout the length of the prosthesis. Consequently, there is no stress concentration, either in the impact phase when the adjacent surface is initially contacted by the wearer of the prosthesis 10, or when return of the accumulated forces stored in the prosthesis 10 is accomplished.

The aforementioned flexure of the foot portions 12 and 14 provides the capacity for increased surface area contact between foot means 32 and the adjacent surface during both the impact and delivery phases of the prosthesis 10. It will be noted that the elongated structure of the portions 12 and 14, together with their aforesaid flexure capabilities, provides for a relatively extended lever arm which achieves stress storage and stress reaction.

The preferred method of manufacturing the forefoot and heel portions 12 and 14 of the prosthesis 10 is by a thermosetting molding process including the utilization of molds having properly shaped and sized cavities. The cavities are designed to receive the requisite number of laminates and the proper volume of polymer, such that the portions 12 and 14 are respectively unitary structures, with the various sections thereof formed simultaneously within each respective portion.

Unlike prior art unitary devices, the fitting of the prosthesis 10 involves the judicious adjustment of the prosthesis by the proper combination of forefoot and heel portions 12 and 14. Only when the proper correlation has been accomplished, can the cosmetic shroud be installed upon the assembled, respective portions of the prosthesis 10.

By the prosthesis of my invention I provide a foot prosthesis which can be carefully matched to the weight, stride and physical characteristics of the wearer. This is accomplished by carefully balancing the respective physical characteristics of the forefoot and heel portions 12 and 14 and the various sections thereof.

Moreover, the assembled prosthesis is far lighter in weight than prior art prostheses since the inherent design and structure of the prosthesis, the materials used and the careful calculation of stress factors of the components of the prosthesis permit fine-tuning of the prosthesis to the needs of the wearer thereof.

The prosthesis of my invention has been described with some particularity but the specific designs and constructions disclosed are not to be taken as delimiting of the invention in that various obvious modifications will at once make themselves apparent to those of ordinary skill in the art, all of which will not depart from the essence of the invention and all such changes and modifications are intended to be encompassed within the appended claims.

I claim:

1. A Symes foot prosthesis for an amputee who has undergone a Symes amputation in which the amputee's foot is severed from the amputee's leg near the amputee's ankle region, said prosthesis comprising:

a socket member sized and shaped to receive the stump of said amputee, said socket member having a substantially vertically oriented attachment surface formed along the back side of the lower portion thereof;

a flexible foot member secured to said socket member, said foot member being fabricated of superimposed laminates maintained in operative relationship by an encapsulating polymer such that said foot member is adapted to store and release energy during normal walking and running activities, said foot member comprising:

a substantially vertically oriented attachment section for detachably securing said foot member to said socket member, said attachment section having a substantially vertically oriented attachment surface adapted to mate with said attachment surface of said socket member such that said foot member may be secured to said socket member;

a curvilinear ankle section formed continuously with and extending downward and forward from said attachment section, said ankle section being adapted to store and release energy and having a substantially smooth radius of curvature ranging between ¾ inches and 1-¾ inches;

a toe section formed integrally with and extending relatively forward from said ankle section, said toe section being adapted to store and release energy and to provide substantially the sole means of support for all vertical, transverse and torsional forces transmitted to said foot member during toe-off; and a heel section extending rearwardly from said ankle section, said heel section being adapted to store and release energy and to provide substantially the sole means of support for all vertical, transverse and torsional forces transmitted to said foot member during heel strike;

said socket member being attached to said attachment section of said foot member such that the lower extremity of said socket member is positioned just below the location of the residual Symes ankle joint.

* * * * *